(12) United States Patent
vanDijk et al.

(10) Patent No.: US 10,200,072 B2
(45) Date of Patent: Feb. 5, 2019

(54) PORTABLE DEVICE

(71) Applicant: Mitel Networks Corporation, Ottawa (CA)

(72) Inventors: Wilco vanDijk, IJsselstein (NL); Martijn Schuurmans, Den Bosh (NL)

(73) Assignee: Mitel Networks Corporation, Ottawa, Ontario (CA)

( * ) Notice: Subject to any disclaimer, the term of this patent is extended or adjusted under 35 U.S.C. 154(b) by 0 days.

(21) Appl. No.: 15/464,184

(22) Filed: Mar. 20, 2017

(65) Prior Publication Data

US 2017/0279474 A1 Sep. 28, 2017

(30) Foreign Application Priority Data

Mar. 23, 2016 (EP) ..................... 16161969

(51) Int. Cl.
| | | |
|---|---|---|
| *H04W 76/14* | (2018.01) | |
| *H04B 1/3827* | (2015.01) | |
| *H04L 29/08* | (2006.01) | |
| *A61B 5/00* | (2006.01) | |
| *H04W 4/80* | (2018.01) | |
| *H04W 76/30* | (2018.01) | |
| *A61B 5/11* | (2006.01) | |

(52) U.S. Cl.
CPC ............. *H04B 1/385* (2013.01); *A61B 5/00* (2013.01); *A61B 5/0002* (2013.01); *A61B 5/0015* (2013.01); *H04L 67/22* (2013.01); *H04W 4/80* (2018.02); *H04W 76/14* (2018.02); *H04W 76/30* (2018.02); *A61B 5/1113* (2013.01); *A61B 2560/0456* (2013.01)

(58) Field of Classification Search
USPC .................... 455/574, 343.1–343.6
See application file for complete search history.

(56) References Cited

U.S. PATENT DOCUMENTS

| 8,878,749 B1 * | 11/2014 | Wu .................. G01S 17/06 |
|---|---|---|
| | | 345/8 |
| 9,544,408 B2 * | 1/2017 | Liang ................ H04M 1/21 |
| 2005/0283661 A1 * | 12/2005 | Wong ............... G06F 11/0742 |
| | | 714/12 |

(Continued)

FOREIGN PATENT DOCUMENTS

| EP | 2750361 A1 | 7/2014 |
|---|---|---|
| WO | WO 2006/102538 A2 | 9/2006 |
| WO | WO 2010/051001 A1 | 5/2010 |

*Primary Examiner* — Lana N Le (57) ABSTRACT

There is provided a portable device (2) for wirelessly communicating with a remote further device (4). The portable device comprises a power source (6) chargeable by a power supply (8) separate from the portable device. The portable device is configured to have a plurality of coupling states associated with the power supply. The power supply is separate from the device and remote from the further device. The portable device also comprises communication apparatus (10) wirelessly connectable to the further device and configured to enable the portable device to have a wireless connection state associated with the further device. A processor (12) is configured to monitor a change between a first and a second of the said coupling states; and, output data for changing the connection state based upon the change from the first coupling state to the second coupling state.

11 Claims, 6 Drawing Sheets

(56) References Cited

U.S. PATENT DOCUMENTS

| | | | |
|---|---|---|---|
| 2005/0286274 A1* | 12/2005 | Pfitzer | G01R 31/40 363/37 |
| 2006/0218421 A1* | 9/2006 | Camagna | H04L 12/10 713/300 |
| 2008/0002355 A1* | 1/2008 | Carnevali | G06F 1/1632 361/679.41 |
| 2010/0261510 A1* | 10/2010 | Rajamani | H04W 36/385 455/574 |
| 2012/0242168 A1* | 9/2012 | Tsai | H04L 12/10 307/112 |
| 2012/0262558 A1* | 10/2012 | Boger | G02B 27/0093 348/61 |
| 2013/0254579 A1* | 9/2013 | Derbyshire | G06F 1/3212 713/340 |
| 2013/0300636 A1* | 11/2013 | Cunningham | G10L 13/02 345/8 |
| 2015/0078756 A1* | 3/2015 | Soto | H04B 10/808 398/116 |
| 2015/0358452 A1* | 12/2015 | Kranz | A61B 5/681 455/557 |

* cited by examiner

PORTABLE DEVICE

CROSS REFERENCE TO RELATED APPLICATION

This application claims the benefit and priority of European Patent Application No. EP 16161969.7 entitled "PORTABLE DEVICE," filed on Mar. 23, 2016, the contents of which are hereby incorporated herein by reference.

FIELD OF THE INVENTION

The present invention is in the field of devices, in particular portable devices configured to wirelessly communicate with other devices.

BACKGROUND

Portable devices are used by a variety of people. Several types of devices exist including mobile phones, smart phones, tablets and pagers. Different types of portable devices are typically intended to be used for different purposes or in different environments. Some of these purposes include for personal use and for use in a particular working environment. When in a working environment, such as a healthcare environment, a user may be required to use his or her hands in a continual manner and therefore may not be able to pick up and check the device regularly. If work related information or instructions are being relayed to the user via a portable device, then the user may need to check the device for the instructions. Sometimes these instructions may be time critical and require the user to review them immediately. This may pose a problem if the user is trying to view these instructions from a smart phone display which the user carries in their pocket because the user may be using both hands to carry out a work task that cannot be interrupted. Also, the user may be working in an environment where the spread of infection should be minimised. Continually picking up and looking at a device for instructions may increase the spread of infection. Some working environments have multiple people working within them wherein each person may need to be given separate and different instructions. These environments may also require different people to work on different shifts. Some current workplace solutions may address this by each person having their own portable device, such as a smart phone or a pager. It may be costly to provide each worker with their own separate device to receive information on, particularly if the workforce is a large one. US2013/0344812 A1 describes a method for enabling a wireless communication between at least one peripheral unit (referenced as Bluetooth slaves 'al-aN') and a wireless device (referenced as '100') by using a docking station (refereed as '10'). The docking station and the peripheral units al-aN form at least part of a wireless docking environment for the wireless device. The Bluetooth slaves al-aN are paired with a main Bluetooth master of the docking station. The main Bluetooth master of the docking station 10 thereby contains the Bluetooth slaves pairing information. When the device enters the wireless docking environment and happens to be in reach and listening, it starts communicating with the docking station, using a second communication type such as Wi-Fi. The pairing of the wireless device to the docking station produces a "successful docking" event and the wireless device 100 becomes a docked device. Once the Wi-Fi connection is established, the docking station is able to send the Bluetooth pairing information to the docked wireless device. The Bluetooth pairing information contains the data suitable for communicating with the Bluetooth slaves al-aN. US2013/0344812 A1 does not describe the coupling of the device to a power supply.

U.S. Pat. No. 7,249,212B2 describes a method and system for wirelessly coupling a computer with a peripheral device. The peripheral device is initially docked to a docking port in the computer. Detecting the docking event, the computer then turns on the docked peripheral device and listens for identifiers from all peripheral devices within range of the computer, including the identifier for the peripheral device that is presently docked with the computer. The computer then instructs the docked peripheral device to 'turn off', thus preventing the docked peripheral device from broadcasting its identifier. By a process of deduction, the computer is able to identify the docked peripheral device.

SUMMARY

According to a first aspect of the present invention, there is provided a portable device for wirelessly communicating with a remote further device; the portable device comprising: a power source chargeable by a power supply separate from the portable device; the portable device configured to have a plurality of coupling states associated with the power supply; the power supply being separate from the device and remote from the further device; communication apparatus wirelessly connectable to the further device and configured to enable the device to have a wireless connection state associated with the further device; a processor configured to: monitor a change between a first and a second of the said coupling states; and, output data for changing the connection state based upon the change from the first coupling state to the second coupling state. The first aspect may be configured such that one of the said first and second coupling states allows for the power source to be charged by the power supply whilst the other of the said first and second coupling states does not allow the power source to be charged by the power supply.

The first aspect may be modified in any suitable way as disclosed herein including but not limited to any one or more of the following.

The portable device may comprise an antimicrobial material. The portable device may comprise an antimicrobial surface, for example an outer surface contactable by a user. The portable device may be configured such that the communication apparatus is wirelessly connectable to the further device via a personal area network, PAN. The portable device may be configured such that the power source comprises a capacitor.

The portable device may be configured such that the said data output from the processor comprises data configured to cause the communication apparatus to wirelessly connect or disconnect from the further device.

The portable device may be configured such that: the first coupling state is associated with the power source being coupled to the power supply; the second coupling state is associated with the power source being uncoupled to the power supply.

The portable device may be configured such that the processor is configured to output data for at least one of: initiating the un-pairing of the portable device from the further device upon a change from the second coupling state to the first coupling state; initiating the pairing of the portable device to the further device upon a change from the first coupling state to the second coupling state.

The portable device may comprise a display for outputting information associated with data received from the further device.

The portable device may be configured such that the output data comprises connection data associated with establishing a secure connection with the further device; the device configured to output information from the display associated with connection data.

The portable device may be configured such that the portable device is attachable about the torso of a user.

The portable device may be configured such that the portable device is configured to remove data associated with the pairing upon the device and further device becoming unpaired.

According to a second aspect of the present invention, there is provided a system comprising the portable device as described in the first aspect, the system further comprising any one or more of: the power supply as described in the first aspect; a second further device remote from the portable device and further device; the second further device configured to be wirelessly connectable to the further device.

The second aspect may be modified in any suitable way as disclosed herein including but not limited to any one or more of the following.

The system may comprise a second further device, wherein: the second further device is configured to send data to the further device; wherein the further device is configured to send further data to the portable device; the further data associated with the data received by the further device.

The system may comprise a plurality of said portable devices; each portable device associated with and wirelessly connectable to a separate further device; the second further device configured to send further data to each further device; wherein each further device is configured to send further data to its respective portable device.

According to a third aspect of the present invention, there is provided a portable device attachable about the torso of a user, the device comprising: a display configurable to at least partially face the head of the user when the device is attached about the torso of the user; and, communication apparatus configured to receive data from a further device via a wireless personal area network connection, the data for use in displaying information on the display.

The third aspect may be modified in any suitable way as disclosed herein including but not limited to any one or more of the optional features according to the first aspect and/or any of the following.

The portable device may be configured such that communication apparatus is configured to be in one of at least two connection states associated with the further device; the portable device comprising: a power source chargeable by a power supply separate from the portable device; the portable device configured to have a plurality of coupling states associated with the power supply; a processor configured to: monitor a change between a first and a second of the said coupling states; and, output data for changing the connection state based upon the change from the first coupling state to the second coupling state. The portable device may be configured such that one of the said first and second coupling states allows for the power source to be charged by the power supply whilst the other of the said first and second coupling states does not allow the power source to be charged by the power supply.

BRIEF DESCRIPTION OF THE DRAWINGS

Embodiments of the present invention will now be described in detail with reference to the accompanying drawings, in which.

DETAILED DESCRIPTION

Figure 1:
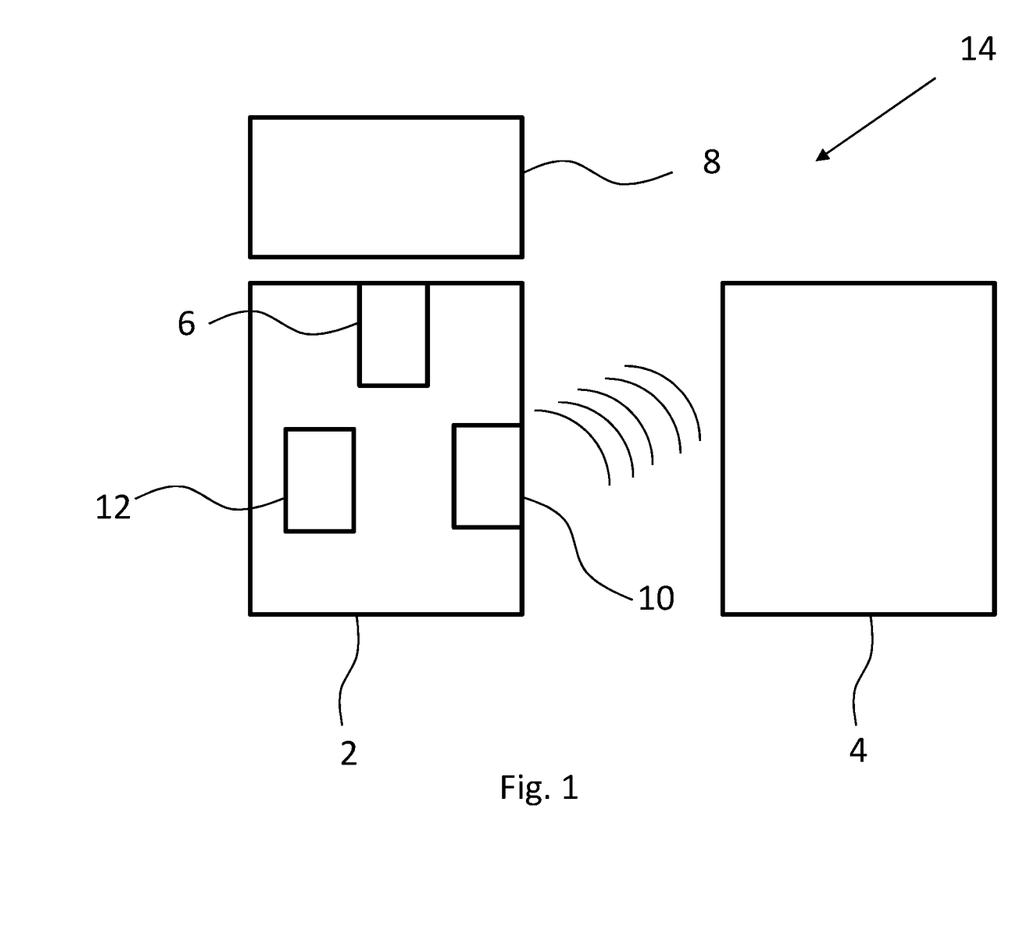
FIG. 1 shows an example of a device for communicating with a further device and coupling with a power supply.

There is presented herein a device for wirelessly communicating with a remote further device. The device may be a portable device. An example of such a device is shown in FIG. 1. The device 2 comprises a power source 6 chargeable by an external power supply 8. The device 2 is configured to have a plurality of coupling states associated with the power supply 8. In use, the device may be in any one of the plurality of coupling states at any given time. The device 2 also comprises a communication apparatus 10 that is wirelessly connectable to the further device 4 and configured to be in one of at least two connection states associated with the further device 4. The device 2 also comprises a processor 12. The processor 12 is configured to monitor for a change between a first and a second coupling state and is preferably configured to operate while the device 2 is in a first and a second coupling state. One of the said first and second coupling states may allow for the power source to be charged by the power supply whilst the other of the said first and second coupling states may be such that it does not allow the power source to be charged by the power supply. The processor 12 is also configured to output data for changing the connection state based upon a change from the first coupling state to the second coupling state.

Figure 2:
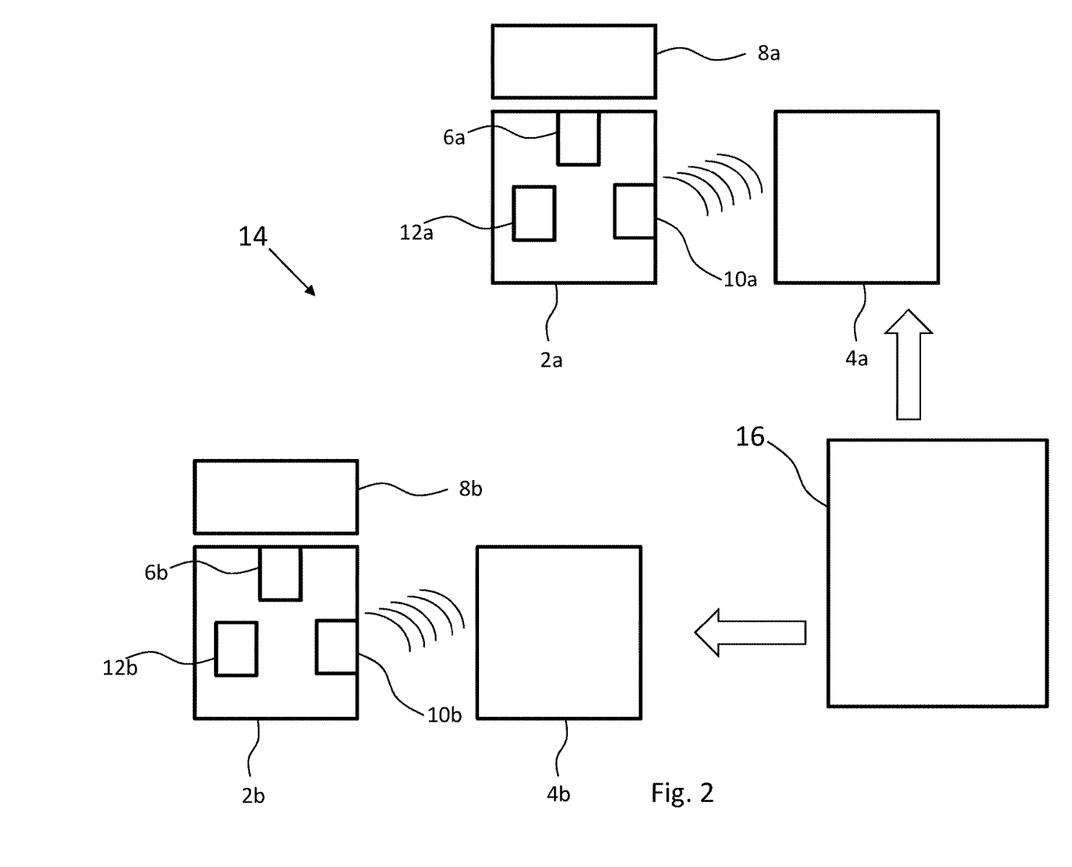
FIG. 2 shows an example of two devices similar to that shown in FIG. 1 wherein each device is in wireless communication with a separate further device and coupled to a power supply.

The device may form part of a system 14 that comprises one or more further devices and/or or more external power supplies. An example of a system 14 that has a two devices 8a/8b; two further devices 4a/4b and two power supplies 8a/8b is shown in FIG. 2.

There is also provided a method for operating a device 2 as described above. The method comprises the steps of determining a change in coupling state from the first coupling state to the second coupling state and then outputting data for changing the connecting state based upon the change from the first coupling state to the second coupling state.

When a person uses the device, for example, the device may therefore be connected or unconnected to the further device. In the unconnected state the device does not receive any data from the further device and in the connected state the device may receive data. A connected or unconnected state may be present when the device is in a coupled or uncoupled state with the power supply 8 (which may be a charger). When the charging coupling state changes, for example from being charged by the external power supply to not being charged, the processor outputs data for changing the wireless connection state with the further device. This may be, for example, sending out a wireless broadcast signal searching for further devices to connect to and/or generating a security code that the user can use to securely connect the device with the further device.

The device may be used in any suitable environment or for any suitable purpose, for example, but not limited to the healthcare environment. In one example, the device may be residing in a coupled state with the power supply (for example being connected to it and being charged by it) and have an unconnected state with the further device. The user may uncouple the device from the external power supply by physically removing the device and attaching it to the clothing surrounding their torso. Upon being uncoupled, the processor initiates a connection process whereby it connects to the further device. Once connected to the further device 4 the device 2 may receive information from the further device 4. This information may be generated from the further device 4 or be based upon data received by the further device 4 from a second further device such as a central server 16 with wireless communication apparatus. The information received by the device 2 may be displayed or otherwise output from the device 2 to the user. The information may be, for example, details of an emergency to go to or a notification of a patient that needs attention. The further device 4 may, for example, be the user's mobile phone which receives information from a second further device 16 such as a central server that sends information to a plurality of users, each user having their own device 2 wirelessly connected to their mobile phone. Once the user has finished using the device 2 they may physically locate the device 2 in a coupled state with the external power supply 8. The power supply 8 may be the same power supply 8 or a different power supply to the one that uncoupled the device from previously). Upon changing from an uncoupled charging state to a coupled charging state, the processor 12 causes the communication apparatus 10 in the device 2 to disconnect from the further device 4 so that the device 2 does not receive further information from the further device 4.

The further device 4 may be a device already carried by the user, such as the user's mobile phone. This allows the system of providing information to the user to use the capabilities of the mobile device to facilitate the transfer of the information. The further device 4 may have a longer range for receiving data from a central server than the device 2. The further device 4 may have processing capability to process data that is superior to that of the device 2. It may have memory to store software that can perform certain functions or calculate parameters and values for the working environment that may in turn be sent to the device 2. It may be associated or have identification information associated with the user which enables the central server 16 to correctly route data to the user which in turn is given to the user via the device 2. The device 2 may therefore be made simply and cheaply and may be small in size as some of the facilities and capabilities for establishing a communications link between a central server (or other centralised system managing data sent to the device)) to the device 2 is catered for by using the further device 4. This further device 4 may also be termed an interim device.

The device 2 and the method may be modified or adapted according to any of the examples and optional features/ modifications described herein. Any features or configurations of any of the examples described herein may be used in other examples where technically appropriate.

Figures 3A, 3B:
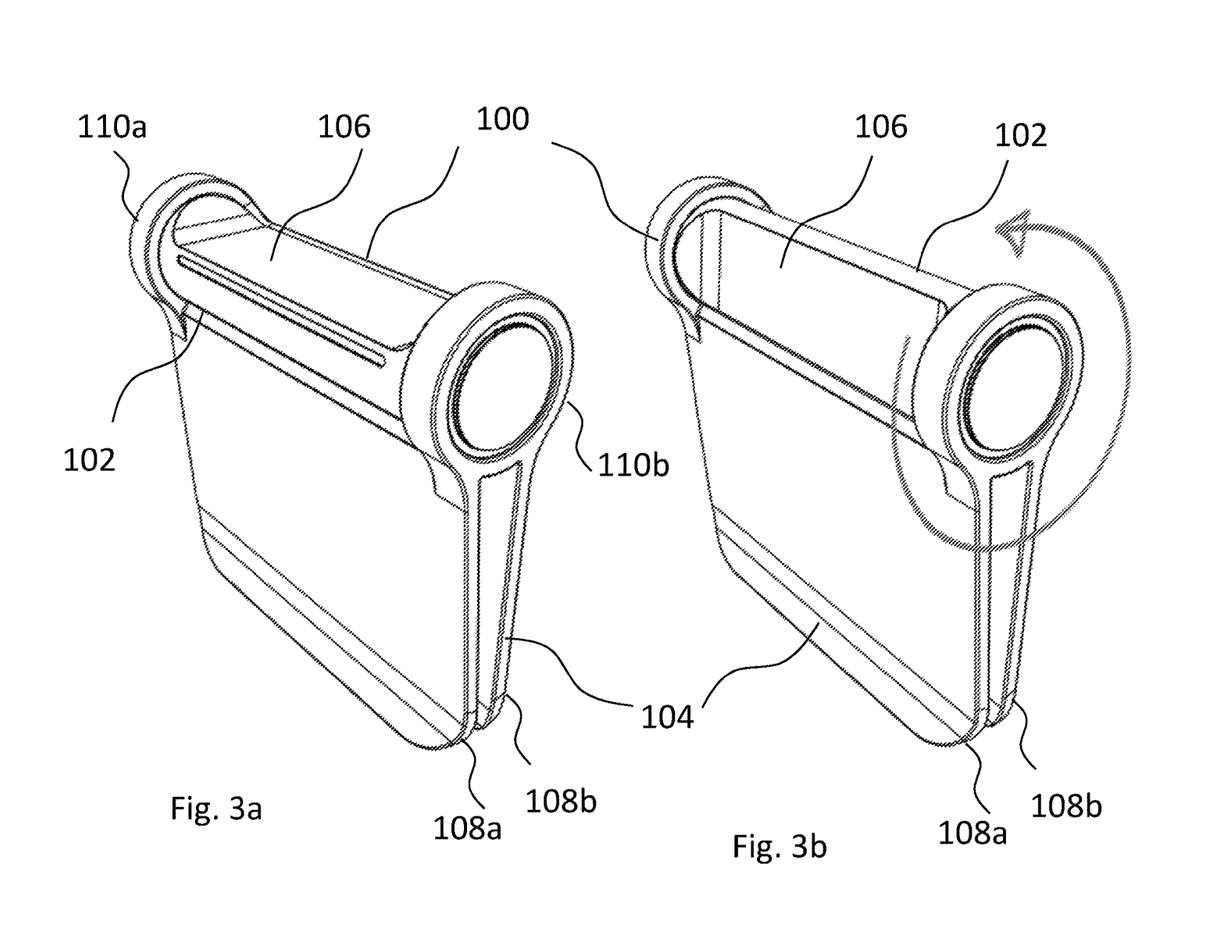
FIG. 3a shows an example of a portable device as described herein and having an attachment means.
FIG. 3b shows the device of FIG. 3a having its display rotated.

The device 2 may be any suitable device, preferably an electrical device using electrical/electronic or optical components such as a memory device, one or more user inputs such as a touch screen or a mechanical button or microphone for voice controlled input. The memory device may be any type of memory or storage media for code and data storage, for example RAM, ROM, EEPROM, cache memory, disk drives, etc. The device 2 preferably has one or more outputs such as a display, a loudspeaker or a headphone socket for the user to plug in a suitable set of headphones. A device 2 may have an audio input device and audio output device so a user can provide and receive verbal communications via the device in a hands free manner. This may include having a Bluetooth® voice profile. The device 2 may be configured to run one or more software modules or have dedicated hardware configured to give rise to the methods described herein and the operation of the device 2 described herein. The software may be run on an operating system. An example of a device 2 with a display is shown in FIGS. 3*a* and 3*b* which show a device 100 having a display 106 that can rotate.

The device 2 may also be a portable device. The portable device in one example has attachment means for securing the device 2 to the user either directly (for example a watch) or indirectly by being attachable to a garment that the user is wearing. The device 2 may integrally incorporate these attachment means or it may be separable from but securable to the said attachment means. The attachment means may be any suitable attachment device or mechanism including a clip or other fasting device such as a hook and loop fastener. Preferably the device 2 is configured to be attached about the torso of a user. If the device 2 further comprises a display, the display is preferably a top display that can be viewed by the user whilst the user is wearing the device 2 on their torso. For purposes of clarity, the torso is intended to be the trunk of a human body independent of head or limbs. When attached to the torso of the user, the user may need to adjust their head to view the top display. This is advantageous in environments where the user should be minimising their hand contact with the device 2 such as a medical environment and environments where the user's hands are normally occupied. The device 2 may be attached to the front portion of a garment covering the user's chest wherein the user looks down to view the display. The display may be adjustable to face different positions.

The device 2 may be configured to output a signal to notify the user of incoming/received information from the further device 4. This may be, for example, an audible signal and/or a haptic effect such as a vibration.

The remote further device 4 is configured to connect wirelessly with the device 2. This remote further device 4 may have any of the components or features described with respect to the device 2. The further device 4 may be portable, such as a tablet or smart phone or may not be portable. The further device 4 typically comprises a processor, a memory device and one or more sets of communication apparatus. The communication apparatus in the remote further device 4 is complementary to the communication apparatus 10 in the device 2 such that communications can be exchanged. The same or a further set of communication apparatus in the further device 4 may be configured to receive information (from another source) and send information to the device 2 based on this received information. For example, a further wireless network such as a mobile network or Wi-Fi may be used by the further device 4 to receive information. The information may be transmitted by this network to the further device 4 from another further device 16 such as a central server. The central server or other equivalent device/devices may be part of a system providing notifications to one or more devices 2. Additionally or alternatively the system may manage communications sent to/from one or more devices 2. The further device 4 may receive the information and send the information directly to the device 2 or it may, alternatively perform processing on the information and send the further processed information to the device 2.

Figure 4:
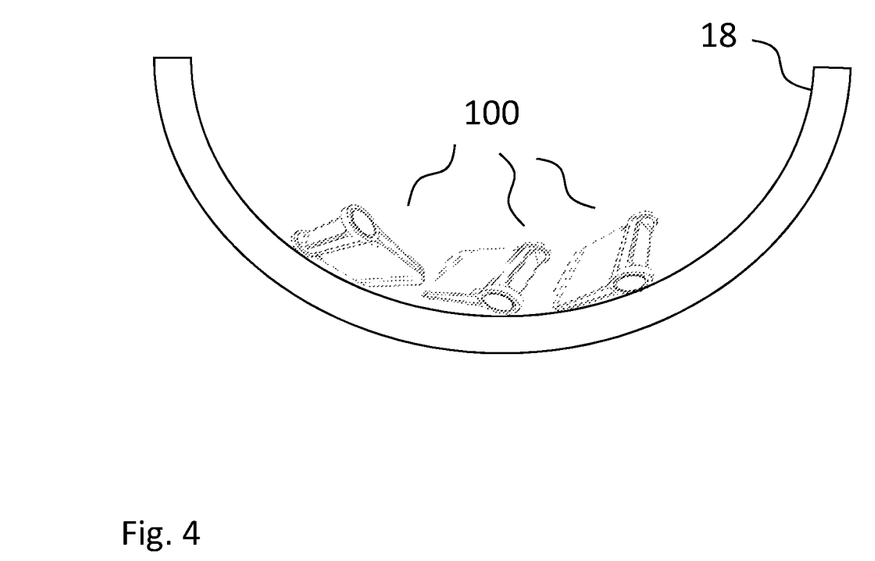
FIG. 4 shows an example of a plurality of devices described herein being inductively charged within a container.

The power source 6 may be any suitable power source 6 that can operate and supply power to the components of the device 2, for example, supplying power to the processor 12 and communication apparatus 10. The power source 6 is configured to be able to deliver power to such components when disconnected or otherwise uncoupled from the external power supply 8. When the portable device 2 is coupled with the power supply 8 the coupled state may allow for the power supply 8 to deliver electrical charge to the power source 6. This may also be referred to herein as 'operatively coupled'. The power source 6 therefore is configured to retain power, preferably electrical power. An example of such a power source 6 is a battery or a capacitor. A capacitor is typically cheaper and smaller than a battery and can be used to power the device 2 because of the minimal amount of processing power required to use the device 2. A capacitor can also be rapidly charged and typically has a longer service life than a battery. The battery is preferably rechargeable such that the external power supply 8 may recharge the battery when the device 2 is coupled to the power supply. The device 2 may have a mechanical socket or interface for mechanically coupling to the power supply 8. In addition or alternatively, the device 2 may be inductively charged via the external power supply 8 when the power source 6 comes into proximity with the power supply 8. An example of this is shown in FIG. 4 where a plurality of the devices 100 in FIG. 3a/3b are placed in an open topped container 18 which is used to inductively charge the devices 100.

The device 2 may comprise one or more power sources 6, for example the device 2 may comprise a battery for storing electrical charge and one or more modules/devices for generating electrical power from light such as a solar module.

The external power supply 8 may be any suitable power supply that can couple to the device 2 and charge the power source 6. A preferred power supply 8 is a charger. As previously described for the power source 6, the power supply may be connected to the device 2 via a type of mechanical coupling or another type of coupling including inductive coupling. The external power supply 8 may be a docket that the device 2 may attach to or be housed within when the user wishes the device 2 to be coupled to the power supply 8 and charge the power source 6.

The coupling state between the device 2 and the external power supply 8 may be any suitable coupling including a mechanical state associated with the physical connection of the device 2 to the external power supply 8. The coupling state may comprise a charging state associated with the power source 6 receiving power from the power supply 8. The coupling state may be a connected state or unconnected state in one particular example. In another example the coupling state may comprise a charging state, and a non-charging state. The processor 12 may receive information associated with the change in coupling state by using any suitable means. For example, monitoring the battery charge and determining whether or not the battery charge is increasing or decreasing or staying constant. In one example, if the battery charge is increasing then the processor 12 can determine that the device 2 has a coupled state with the power supply 8. Correspondingly if the power source 6 is decreasing in charge or otherwise staying at a non-fully charged state and not decreasing, the processor 12 may determine that the device 2 is in an uncoupled state with the external power supply 8. The monitoring of the coupling state may be performed using the processor and/or any other suitable hardware or software within the device 2. One example is a mechanical device such as a latch mechanism to detect the mechanical connection to the charging device 8.

The communication apparatus 10 associated with the device 2 may be housed within the device 2 or alternatively coupled to it. The communication apparatus 10 may comprise a wireless transmitter, wireless receiver or wireless transceiver. The communication apparatus 10 is preferably capable of transmitting and receiving data to and from the further device 4. The communication apparatus 10 is preferably controlled by the processor 12 running a software application operating a communication protocol/method that enables the device 2 to connect and communicate with the further device 4. The communication apparatus 10 may output one or more signals to establish a wireless connection with the further device 4. Preferably, the wireless connection is established using secured methods or means such as an encrypted connection and/or a connection requiring a security code or pin, examples of which are described later. One example of establishing a connection between the communication apparatus 10 and the further device 4 includes pairing the device 2 with the further device 4 before sending data between them.

The wireless connection between the device 2 and further device 4 may be via network of two or more devices networked together so that at least one device 2/4 may receive information from the other device 2/4. In one preferred example, the network is a wireless personal area network (PAN). Examples of wireless PAN's include Bluetooth® and infrared communications governed by the infrared data association. In one example, the communications between the connected communication apparatus 10 and the further device 4 are via wireless UHF radio waves between 2.4 to 2.485 GHz. When using Bluetooth® technology, the device 2 may act as a master Bluetooth device that can communication with the further device 4 via a Piconet.

The processor 12 may be any suitable data processing device capable of giving effect to the steps described herein. Examples of processors 12 include electronic processors such as an Intel® processor. The processor 12 may be operatively connected (for example by wires or other electrical connections) to one or more modules such as memory modules, controllers and other apparatus of the device 2. The processor 12 may be used to run software such as an operating system and/or applications that allow the processor 12 to perform its functions as described herein. The processor 12 may include a plurality of processors and/or may include dedicated hardware configured to perform the functions of the processor 12.

In one preferred example, including examples using Bluetooth® technology, the processor 12 determines the change in coupling state between the device 2 and the power supply 8 and then initiates a connection between the device 2 (via the communication apparatus 10) and the further device 4. This may be achieved using suitable Bluetooth® communication protocols. The communication apparatus 10 may be instructed to search for other local Bluetooth devices in the immediate personal area of the device 2 and generating a pin code that is output to the user (for example by a display or loudspeaker). The user then manually accesses the further device 4 to confirm the connection request from the device 2 and then inputs the code into the further device 4 to securely link the two devices 2/4 (for example by pairing them). When the devices 2/4 are connected, they may have a connection state of "connected" or "paired". When the device 2 and further device 4 are not connected (i.e. not able to send communications between each other) then the connection state may be termed "unconnected", "unpaired" or "disconnected".

Figure 5A:
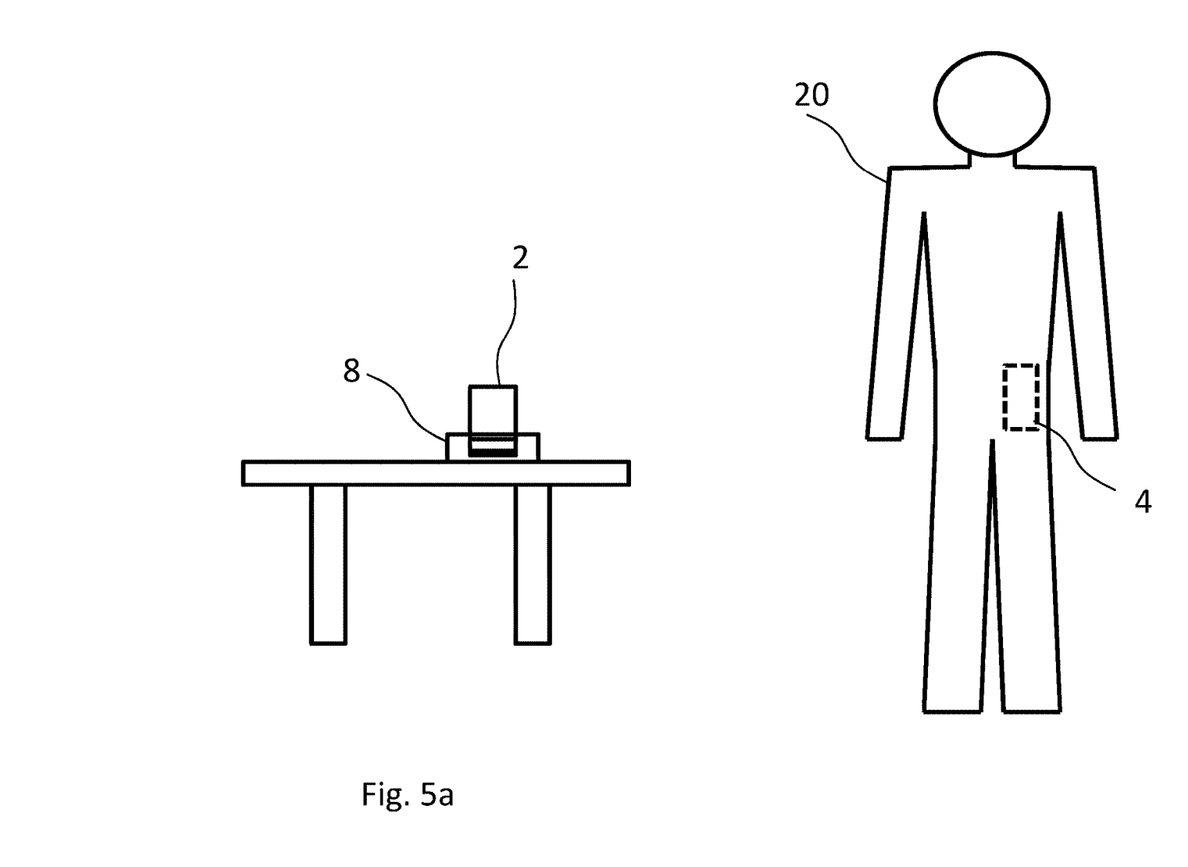
FIG. 5a shows an example of a user carrying the further device wherein the device is located upon, and being charged by, a charger.

In one example, the processor 12 outputs the data for changing from an unconnected state to a connected state when the device changes from a coupled state with the power supply 8 to an uncoupled state with the power supply 8. An example of using this particular feature would be a healthcare worker picking up a device 2 on charge with the external power supply 8. FIG. 5a shows an example where a healthcare worker 20 is carrying a smart phone. This smart phone is the further device 4 in this example. This phone is a personal phone and has software to establish a secure link with the device 2. In FIG. 5a, the device 2 is docketed in a charger 8 which is supplying electrical charge to the device's power source 6 (not shown). The device 2 contains no data about the smart phone 4, including having no previously generated or stored codes or keys associated with a previous wireless connection resulting from a previous pairing with the smart phone or any other further device 4. The device 2 in FIG. 5a is similar to the device 100 shown in FIGS. 3a/3b. Upon picking up the device, the power source 6 ceases to be charged by the power supply 8. Therefore, the device 2 changes state from a coupled state to an uncoupled state. The user has his or her mobile (smart) phone in their pocket. This mobile phone has complementary communication apparatus and means to the communication apparatus 10 in the device 2, such that a wireless connection between the device 2 and further device 4 may be made. In this example, the communication apparatus 10 includes a Bluetooth® transmitter and receiver apparatus. The user 20 attached the device 2 to their clothing, preferably upon their torso, such as the chest area, and rotates the device display so that he/she can view the display by simply moving his/her head downwardly. The processor 12 monitors the change in charging coupling and determines the device 2 is now uncoupled.

Figure 5B:
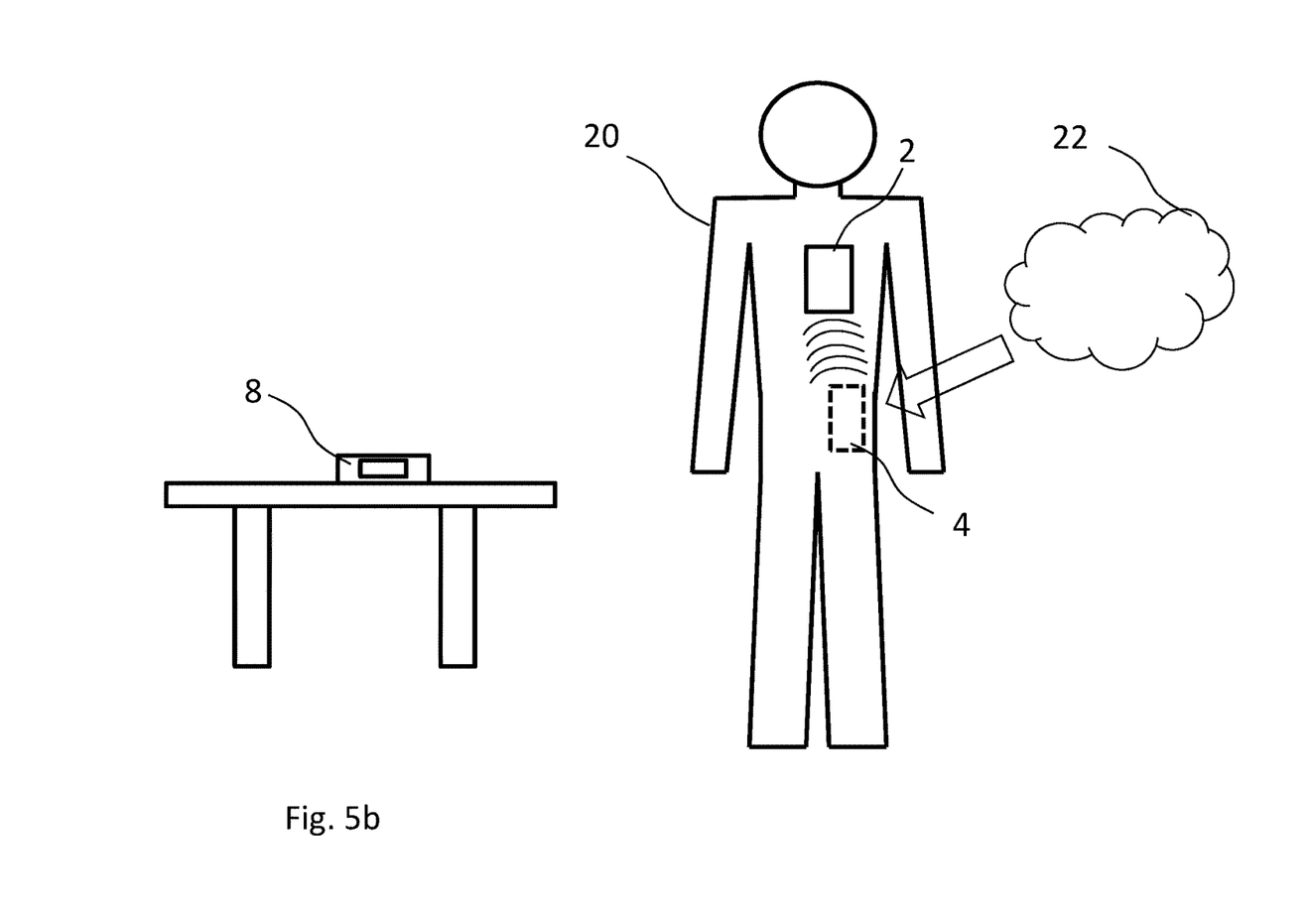
FIG. 5b shows the example of FIG. 5a wherein the user has removed the device from the charger and attached it to the front of their torso; the device and further device in wireless connection and the further device receiving data from a network.

Upon the change in coupling state, the processor 12 searches for local devices and finds a plurality of devices 4 to connect to including the mobile smartphone. The user 20 interacts with the smart phone to accept/select the connection with the device 2. The processor also outputs a pin code on the device's display. This may be a pre-determined code or one that is randomly generated. Randomly generated codes are useful in helping to distinguish between multiple devices 2 performing the same connection process. The user reads the code and inputs the code into the smart phone 4 via a user interface such as a keypad or touchpad. Once the devices 2/4 have been securely linked using the pin code, the mobile phone 4 may therefore be used as a hub for another further device/system (such as a communication management system run by a server 16, not shown in FIG. 5b) to send information to the device 2 via the hub. The smart phone may communicate with the management system via a network 22 such as the internet or a local area network. Furthermore, once a secure link has been made between the device 2 and further device 4 (for example by pairing), the device 2 may be configured to be un-connectable to other further devices 4 until it disconnects from its current further device 4. In doing this, a device 2 can only receive communications (using the wireless communication method use to connect to the further device) through a single further device 4 at any one time. The device 2 may therefore inhibit all other pairing attempts once paired with a further device 4. The device 2 may additionally send communications to the central server via the hub, for example: by the user pressing a button on the device 2 to notify the central system of the users presence at a particular work station; or the user providing verbal input into the device which is then sent to the server 16 via the hub. A two-way communication channel may be established between the serer 16 (or other similar management system) and the device 2 via the hub.

FIG. 2 shows a further example of a system 14 wherein a second further device 16 is a server that is configured to send information to two separate further devices 4a/b. These further devices 4a/b are, in this example, personal devices associated with two different users. The personal devices 4a/b in this example may be any suitable device such as a mobile phone or a tablet that is configured to receive communications from the server 16. Each of the further devices 4a/b is carried by its associated user wherein each user also each has a device 2a/b attached about their person or otherwise carried by the user such that the user may easily view a display on the said device 2a/b. In this example, each of the users works in a different area of a building, for example in a different ward of a hospital. The area in which each user works has its own power supply 8a/b so that the user can locally put the device 2a/b on charge. Each of the devices 2a/b is configured to be able to communicate via a wireless personal area network connection to the further device 4a/b. For example, each of these devices may be communicating using Bluetooth® technology.

Each of the further devices 4a/b is associated with user and contains identification information associated with that user. This identification information may be used by the server 16 to determine where information should be sent to. For example, in FIG. 2, one user is carrying further device 4a and device 2a wherein another user is carrying further device 4b and device 2b. The server 16 has information for sending to the user carrying the mobile device 4a. The server initiates a wireless connection between itself and the further device 4a (although a connection may have already been set-up) and sends a communication with the associated information to this further device 4a. In turn, the mobile device 4a then receives this data and then communicates the same data via a Bluetooth® connection to device 2a so that device 2a can output this information upon its display screen.

The system 14 having the server 16 may send other information to the user carrying devices 4b and 2b. In other examples the system may have more than two devices that are fed information from the server 16. The server 16 may be a single server or plurality of servers operating an information distribution system that manages information needing to be sent to different users and sends the correct information to the correct further device 4a/b. The further devices 4a and 4b and other further devices described herein may have a software application that allows the said further device to be used in the system and transfer the relevant information from the server 16 to the associated device 2a or 2b. The software may, for example, when run or activated, initiate a Bluetooth® activation on the further device 4a/b such that the further device 4a/b is capable of being found by devices 2a/b. Furthermore, when this application runs it may look for, or otherwise initiate the connection to, the server 16 and inform the server of the user so that the server knows that the user of further device 4a/b is active and ready to receive information. In another example the user may manually establish the connection between the device 2 and the server 16 by providing a user input into the mobile device 4b so that the further device 4 is connected and receive communications from the device 2. Once this connection has been established, the device 2 then may send a communication to device 4 that in turn initiates a further process in the device 4 to register itself with or log into the communication management system by making a communication to the server 16. Thus, in this example, the setting up of a wireless connection between the further device 4b and the device 2b causes the user to be registered on the system 14.

FIG. 3a shows an example of a portable device 100. The portable device 100 comprises a device 102 having at least the components as shown and described with reference to the device 2 shown in FIG. 1. The portable device 100 also comprises an attachment device 104. The attachment device 104 has two spaced apart annular members 110a and 110b that are each sized to accommodate end portions of the device 204. The device 102 has a substantially longitudinal cylindrical shape wherein each longitudinal end of the device 102 has a substantially circular outer periphery that fits within the inner periphery of the annular members 110a and 110b. The device 102 is therefore permitted to rotate whilst still being housed by the attachment device 104. One part of the device comprises a display 106 running at least partially along the length of the device 102 such that rotation of the device 102 causes the display to change output angle. The attachment device 104 further comprises two securing blades 108a and 108b that extend away from, and connect to, the annular members 110a and 110b. The pair of blades extend substantially in the same direction but narrowing in separation width as they extend from the annular members 110a and 110b. The attachment device 104 is preferably made from a solid material that is resiliently deformable so that the blades may act as a clip that can be used to attach the portable device 100 to a remote object such as a user's front shirt pocket. FIG. 3b shows the device 100 of FIG. 3a where the user has rotate the device 102 to change the angle of view of the display.

As previously described, the device 2 and further device 4 may have a connection state of being paired or unpaired. During pairing, the two devices may establish a relationship by creating a shared secret key. If both devices have access to the key, for example by storing it they may be said to be 'paired' or 'bonded'.

The connection state may therefore be associated with the ability to communicate over a key shared communication link. One state may be a key shared link whilst the other state may be a state where the device 2 and further device 4 do not share keys to permit communications to be transferred between them.

In one example using Bluetooth® technology to connect the device 2 and further device 4, once a key is generated, an authenticated Asynchronous Connection-Less (ACL) link between the device 2 and further device 4 may be encrypted to protect exchanged data against eavesdropping. In a preferred example, when the device 2 changes from an uncoupled charging state to a coupled state with a charger 8, the device deletes the keys from its internal memory, hence removing all details of the previous pairing with the further device 4. The further device 4 may also delete the key either via a process internally initiated by the further device 4 or by an instruction received remotely from a remote device.

The pairing mechanism may be any suitable pairing mechanism, for example, pairing mechanisms according to Bluetooth v2.0 or v2.1.

Pairing may occur by legacy pairing where a PIN code is entered into each device 2/4 and pairing is only successful if both devices 2/4 enter the same PIN code. Pin codes may be any suitable code that is usable and/or input-able into the device 2 or further device 4. For example, they may include a numeric string or an alphanumeric string. One example is a 16-byte UTF-8 string. A pin code may be randomly generated by one of the device 2 or further device 4. Alternatively, one of the device 2 or further device 4 may have a fixed pin code that is hard coded wherein it is this pin code that is used to create the pairing. The generated pin code (for example one generated by the device 2) may be output to the user, for example being displayed, so that the user may manually input the code into the further device 4.

Pairing may be accomplished using Secure Simple Pairing (SSP) by using public key cryptography. SSP may be include numeric comparison wherein a 6-digit numeric code is displayed on each device 2/4. The user compares the numbers to ensure they are identical. If the comparison succeeds, the user confirms pairing on the device(s) 2/4. In such a pairing process the device 2 and further device 4 preferably have a mechanism to accept a user input.

The pairing may also use a passkey entry process. For this process, the device 2 preferably comprises a display or another output device to output a numeric code to the user. For example, the display of the device 2 may be used to show a 6-digit numeric code to the user, who then enters the code on a keypad or other input mechanism of the further device. In the second case, the user of each device enters the same 6-digit number.

The pairing mechanism may use an out of band (OOB) communication process wherein an external means of communication, such as Near Field Communication (NFC) is used to exchange some information used in the pairing process. Pairing is completed using the Bluetooth radio, but requires information from the OOB mechanism.

Any of the keys may be stored on the device 2 or further device 4, however in some examples the processor 12 of the device 2 is configured to remove details of any pairings upon the device 2 being coupled to a charger 8, for example by deleting pairing data stored on a memory device. Furthermore the further device 4 may also delete any previous pairing data when the further device moves out of communication range with the device.

There is also presented herein a portable device for wirelessly communicating with a further external device, wherein the portable device comprises an antimicrobial material. The portable device may be a portable device 2 as described elsewhere herein. The antimicrobial material may form any part of the portable device, for example any one or more of but not limited to the following.

The material may be at least one of the materials forming a casing or housing of the portable device 2.

The material may form part of a surface of the portable device, for example an outer surface configured to be exposed to the environment, for example coming into contact with the user's hand. The antimicrobial surface may be formed by applying a coating or other layer upon a surface of the portable device 2. Additionally or alternatively the antimicrobial surface may be part of a material body that has an antimicrobial agent incorporated within the body. For example, the device may have a case body, housing the internal components of the device, wherein the case body is formed of at least one antimicrobial impregnated material such as an antimicrobial plastic.

The antimicrobial material may comprise a polymeric portion that has been impregnated with an organic dye exhibiting antibacterial properties. Examples of organic dyes may include, but are not limited to: methylene blue, toluidine blue, methylene violet, azure A, azure B, azure C, brilliant cresol blue, thionin, methylene green, bromcresol green, gentian violet, acridine orange, brilliant green, acridine yellow, quinacrine, trypan blue, and trypan red. The plastic material can be prepared by contacting at least a portion of the plastic with a solution containing the organic dye and a reducing agent. A solution with appropriate chemical activation of the organic dye can permeate entirely through the plastic.

The casing of the portable device may be formed by treating a surface of the casing with a plurality of functional groups, attaching a linking group to the functional groups, and attaching an antimicrobial agent to the functional group or to the linking group. In particular this may be accomplished by reacting the functional groups with a linking agent to form attachment sites, the linking agent selected from the group consisting of poly(N-succinimidyl acrylate) (PNSA), polyethyleneimine, polyallylimine, and polymers with an aldehyde functional group, and attaching a solvatochromic dye, an antimicrobial agent, or an alkyl-amino containing compound to the attachment sites. The surface of the casing may be treated with a first antimicrobial oxide layer optionally comprising atoms of a metal or metal alloy forming part of the casing; and atoms of an antimicrobial metal selected from the group consisting of silver, copper, and zinc, and combinations thereof, The portable device 2 may comprise apparatus that is configured to communicate directly and/or indirectly with an external device (also referred to as a monitoring device) wherein the external device is configured to determine the location of the portable device and send the position data to be recorded. The monitoring device may form part of a monitoring system having multiple positions sensors in communication with one or more central hubs that store and process data. The sensor device may be a single device located within a room or a set of devices configured to determine a portable devices position by signal triangulation.

In this example, the said apparatus of the portable device is configured to at least cause the transmission of one or more wireless signals either directly from the apparatus or indirectly to the external device. These signals allow the external monitoring device/system to locate the position portable device. Additionally the one or more signals may contain identification information associated with the current user of the portable device, so that upon receiving the signals the system may determine the position of a particular user. Upon receiving the signals, the position information together with the user information may be stored upon a memory device, for example being stored in a database on a central server of a central hub. This may be useful in an environment where someone wants to know where a particular person is or where they have been. For example a nurse carrying the portable device may have worked for four hours before the doctor arrives. The doctor can then look at the stored data using a user terminal connected to the central server and see where the nurse has been during the last four hours. The doctor may want to do this to check to see that the nurse has been spending an appropriate amount time with a particular patient. The portable device may therefore act as a beacon.

The identity information uploaded to the external device by the portable device may be associated with identity information uploaded to the portable device from the user's mobile phone when the user first picks up the portable device and links it to their mobile. Alternatively the portable device may utilise the mobile phones communication capability to send the signals, in which case the phone may simply tag the identity information to the signal when the portable device instructs the phone to send the position signal.

The portable device may comprise apparatus that enables such communication directly with the external sensor, for example communication apparatus separate to the communication apparatus that connects to the users mobile phone as described herein. Examples of this could be a wireless RF transmitter wherein the transmitter is controlled by a controller in the portable device. The controller may be configured with hardware, and optionally software, to instruct the apparatus to send out signals in a broadcast manner at particular time intervals. Additionally or alternatively the controller may be configured to create a communications channel with a particular external device monitoring for such signals. Such position determining signals may be output from the portable device upon the portable device receiving a signal from an external device indicating to the portable device that it is within a particular range or line of sight to the said external device. An example of an external device/sensor forming part of the monitoring system may be a transceiver. The transceiver may be positioned in various locations within a particular environment, for example multiple transceivers, each located in a fixed position in a separate room of a hospital.

The foregoing description is provided to enable any person skilled in the relevant art to practice the various embodiments described herein. Various modifications to these embodiments will be readily apparent to those skilled in the relevant art, and generic principles defined herein can be applied to other embodiments. Thus, the claims are not intended to be limited to the embodiments shown and described herein, but are to be accorded the full scope consistent with the language of the claims, wherein reference to an element in the singular is not intended to mean "one and only one" unless specifically stated, but rather "one or more." All structural and functional equivalents to the elements of the various embodiments described throughout this disclosure that are known or later come to be known to those of ordinary skill in the relevant art are intended to be encompassed by the claims.

The invention claimed is:

1. A portable device for wirelessly communicating with a remote first further device; the portable device comprising:
   I) a power source chargeable by a power supply separate from the portable device; the portable device configured to have a plurality of coupling states associated with the power supply; the power supply being separate from the device and remote from the further device;
   II) communication apparatus wirelessly connectable to the further device via a personal area network, PAN, and configured to enable the portable device to have a wireless connection state associated with the further device;
   III) a processor configured to:
   monitor a change between a coupled state and an uncoupled state of the said coupling states; wherein the said coupled state is associated with the power source being coupled to the power supply whilst the uncoupled state is associated with the power source being uncoupled to the power supply; and, output data for changing the connection state based upon the change from the coupled state to the uncoupled state; wherein said processor is configured to output data for at least one of:

A) initiating the un-pairing of the portable device from the further device upon a change from the uncoupled state to the coupled state; and B) initiating the pairing of the portable device to the further device upon a change from the coupled state to the uncoupled state.

2. A portable device as claimed in claim 1 wherein the PAN uses radio waves.

3. A portable device as claimed in claim 1 comprising an antimicrobial material.

4. A portable device as claimed in claim 1 wherein the said data output from the
processor comprises data configured to cause the communication apparatus to wirelessly connect or disconnect from the further device.

5. A portable device as claimed in claim 1 comprising a display for outputting information associated with data received from the further device.

6. A portable device as claimed in claim 5 wherein the portable device is attachable about the torso of a user; and, the display is configurable to at least partially face the head of the user when the portable device is attached about the torso of the user.

7. A portable device as claimed in claim 1 wherein the output data comprises connection data associated with establishing a secure connection with the further device: the portable device configured to output information from the display associated with the connection data.

8. A portable device as claimed in claim 1 wherein the portable device is configured to remove data associated with the pairing upon the portable device and further device becoming unpaired.

9. A system comprising the portable device as claimed in claim 1, the system further comprising any one or more of:
the power supply;
a second further device remote from the portable device and the first further device; the second further device configured to be wirelessly connectable to the first further device.

10. A system as claimed in claim 9 comprising the second further device, wherein: the second further device is configured to send data to the first further device; wherein the first further device is configured to send further data to the portable device; the further data associated with the data received by the first further device.

11. A system as claimed in claim 10 comprising a plurality of said portable devices;
each portable device associated with and wirelessly connectable to a separate further device;
the second further device configured to send further data to each further device;
wherein each further device is configured to send further data to its respective portable device.

* * * * *